(12) United States Patent
Hagele

(10) Patent No.: US 6,968,236 B2
(45) Date of Patent: Nov. 22, 2005

(54) CERAMIC CARDIAC ELECTRODES

(75) Inventor: Richard J. Hagele, Honeye Falls, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 609 days.

(21) Appl. No.: 10/058,984

(22) Filed: Jan. 28, 2002

(65) Prior Publication Data
US 2003/0144717 A1 Jul. 31, 2003

(51) Int. Cl.$^7$ ............................................. A61N 1/05
(52) U.S. Cl. ...................... 607/119; 600/372; 600/374; 607/122
(58) Field of Search . 607/119, 122, 126; 600/372–374

(56) References Cited

U.S. PATENT DOCUMENTS

| | | | |
|---|---|---|---|
| 3,057,356 A | 10/1962 | Greatbatch | 128/422 |
| 3,478,746 A | 11/1969 | Greatbatch | 128/421 |
| 3,508,167 A | 4/1970 | Russell, Jr. | 311/111 |
| 3,669,095 A | 6/1972 | Kobayashi et al. | 600/436 |
| 3,686,958 A | 8/1972 | Porter et al. | 73/406 |
| 3,718,142 A | 2/1973 | Mulier | 607/36 |
| 3,789,667 A | 2/1974 | Porter et al. | 73/406 |
| 3,825,015 A | 7/1974 | Berkovits | 607/123 |
| 4,012,641 A | 3/1977 | Brickerd, Jr. et al. | 307/106 |
| 4,041,954 A | 8/1977 | Ohara | 128/419 |
| 4,050,004 A | 9/1977 | Greatbatch | 363/59 |
| 4,071,032 A | 1/1978 | Schulman | 607/36 |
| 4,091,818 A | 5/1978 | Brownlee et al. | 128/419 |
| 4,149,542 A | 4/1979 | Thoren | 607/121 |
| 4,200,110 A | 4/1980 | Peterson et al. | 128/634 |
| 4,210,029 A | 7/1980 | Porter | 73/705 |
| 4,254,776 A | 3/1981 | Tanie et al. | 128/421 |
| 4,325,382 A | 4/1982 | Miodownik | 600/486 |
| 4,333,053 A | 6/1982 | Harrison et al. | 324/307 |
| 4,341,221 A | 7/1982 | Testerman | 600/377 |
| 4,379,262 A | 4/1983 | Young | 324/309 |
| 4,432,363 A | 2/1984 | Kakegawa | 128/419 |
| 4,450,408 A | 5/1984 | Tiemann | 324/318 |
| 4,476,870 A | 10/1984 | Peterson et al. | 128/634 |
| 4,491,768 A | 1/1985 | Slicker | 318/139 |
| 4,506,680 A | * 3/1985 | Stokes | 607/120 |
| 4,545,381 A | 10/1985 | Bournay, Jr. et al. | 607/10 |
| 4,611,127 A | 9/1986 | Ibrahim et al. | 307/116 |
| 4,677,471 A | 6/1987 | Takamura et al. | 348/76 |
| 4,682,596 A | 7/1987 | Bales et al. | 606/39 |
| 4,686,964 A | 8/1987 | Yunoki et al. | 600/109 |
| 4,691,164 A | 9/1987 | Haragashira | 324/322 |
| 4,692,347 A | 9/1987 | Yasuda | 427/491 |

(Continued)

FOREIGN PATENT DOCUMENTS

WO    WO 01/74241    10/2001    .......... G01R 33/34

OTHER PUBLICATIONS

Biomedizinische Technik Band 35; Erganzungsband—1990; A Non-Magnetic, MR-Compatible Pacing Catheter for Clinical Application in Magnetocardiography; pp. 162-163.

(Continued)

Primary Examiner—Carl Layno

(57) ABSTRACT

A cardiac electrode termination pair system that is particularly compatible with Magnetic Resonance Imaging (MRI) procedures. The electrodes include tip and ring electrodes made of a body-compatible ceramic on which is applied via electroplating, sputtered or the like an ultra-thin conductive coating of platinum or titanium or other suitable metal which is compatible with conducting electrical impulses into cardiac tissue. The ring electrode may be adapted for connection to a photonic catheter carrying light signals or a non-photonic catheter carrying electrical signals. The ring (or the tip) may house pulse-delivering components and/or sensing components.

10 Claims, 6 Drawing Sheets

U.S. PATENT DOCUMENTS

| | | | |
|---|---|---|---|
| 4,719,159 A | 1/1988 | Clark et al. .................. 429/159 |
| 4,727,874 A | 3/1988 | Bowers et al. ................ 606/38 |
| 4,763,075 A | 8/1988 | Weigert ...................... 324/318 |
| 4,784,461 A | 11/1988 | Abe et al. ................... 385/112 |
| 4,798,443 A | 1/1989 | Knipe et al. ................ 385/113 |
| 4,800,883 A | 1/1989 | Winstrom ...................... 607/7 |
| 4,804,244 A | 2/1989 | Hasegawa et al. ............ 385/69 |
| 4,827,906 A | 5/1989 | Robicsek et al. ............. 600/17 |
| 4,827,934 A | 5/1989 | Ekwall ......................... 607/9 |
| 4,844,099 A * | 7/1989 | Skalsky et al. ............. 607/120 |
| 4,858,610 A | 8/1989 | Callaghan et al. ........... 607/13 |
| 4,879,992 A | 11/1989 | Nishigaki et al. ........... 600/110 |
| 4,880,004 A | 11/1989 | Baker, Jr. et al. ............ 607/4 |
| 4,903,701 A | 2/1990 | Moore et al. ................ 607/22 |
| 4,911,525 A | 3/1990 | Hicks et al. ................ 385/114 |
| 4,930,521 A | 6/1990 | Metzger et al. ............. 607/145 |
| 4,934,785 A | 6/1990 | Mathis et al. ................ 385/68 |
| 4,987,897 A | 1/1991 | Funke ......................... 607/32 |
| 4,991,590 A | 2/1991 | Shi ............................ 600/480 |
| 5,010,888 A | 4/1991 | Jadvar et al. ............... 600/509 |
| 5,029,588 A | 7/1991 | Yock et al. ................. 600/471 |
| 5,055,810 A | 10/1991 | deLaChapelle et al. ...... 333/262 |
| 5,058,586 A | 10/1991 | Heinze ....................... 128/634 |
| 5,061,680 A | 10/1991 | Paulson et al. ............. 505/162 |
| 5,089,697 A | 2/1992 | Prohaska ................ 250/227.21 |
| 5,113,859 A | 5/1992 | Funke ........................... 607/4 |
| 5,131,409 A | 7/1992 | Lobarev et al. ............. 607/156 |
| 5,154,387 A | 10/1992 | Trailer ........................ 607/124 |
| 5,158,932 A | 10/1992 | Hinshaw et al. ............ 505/162 |
| 5,168,871 A | 12/1992 | Grevious ..................... 607/27 |
| 5,178,149 A | 1/1993 | Imburgia et al. ............ 600/463 |
| 5,214,730 A | 5/1993 | Nagasawa et al. ............ 385/59 |
| 5,217,009 A | 6/1993 | Kronberg ..................... 607/51 |
| 5,217,010 A | 6/1993 | Tsitlik et al. .............. 128/419 |
| 5,226,210 A | 7/1993 | Koskenmaki et al. ....... 29/527.5 |
| 5,240,004 A | 8/1993 | Walinsky et al. ........... 600/467 |
| 5,243,979 A | 9/1993 | Stein et al. .................. 607/20 |
| 5,265,602 A | 11/1993 | Anderson et al. .............. 607/9 |
| 5,267,564 A | 12/1993 | Barcel et al. ............... 600/310 |
| 5,324,310 A | 6/1994 | Greeninger et al. ......... 607/28 |
| 5,330,512 A | 7/1994 | Hauck et al. ................ 607/28 |
| 5,348,010 A | 9/1994 | Schnall et al. .............. 600/422 |
| 5,354,220 A | 10/1994 | Ganguly et al. ............ 439/675 |
| 5,370,668 A | 12/1994 | Shelton ....................... 607/29 |
| 5,387,229 A | 2/1995 | Poore .......................... 607/18 |
| 5,387,232 A | 2/1995 | Trailer ........................ 607/124 |
| 5,402,070 A | 3/1995 | Shelton et al. .............. 324/433 |
| 5,410,413 A | 4/1995 | Sela ............................ 356/446 |
| 5,415,653 A | 5/1995 | Wardle et al. .................. 606/7 |
| 5,425,373 A | 6/1995 | Causey, III ................ 600/510 |
| 5,435,308 A | 7/1995 | Gallup et al. ............... 600/342 |
| 5,435,316 A | 7/1995 | Kruse ......................... 600/510 |
| 5,438,987 A | 8/1995 | Thacker et al. ............. 600/337 |
| 5,445,151 A | 8/1995 | Darrow et al. .............. 600/419 |
| 5,453,838 A | 9/1995 | Danielian et al. ........... 356/600 |
| 5,454,837 A | 10/1995 | Lindegren et al. .............. 607/9 |
| 5,456,698 A | 10/1995 | Byland et al. ............... 607/36 |
| 5,464,014 A | 11/1995 | Sugahara ..................... 600/411 |
| 5,476,095 A | 12/1995 | Schnall et al. .............. 600/423 |
| 5,520,190 A | 5/1996 | Benedict et al. ............ 128/700 |
| 5,523,534 A | 6/1996 | Meister et al. ................ 174/36 |
| 5,569,158 A | 10/1996 | Suzuki et al. ............... 600/110 |
| 5,570,671 A | 11/1996 | Hickey ....................... 600/486 |
| 5,574,811 A | 11/1996 | Bricheno et al. ............. 385/52 |
| 5,575,772 A | 11/1996 | Lennox .................... 604/96.01 |
| 5,582,170 A | 12/1996 | Soller ......................... 600/322 |
| 5,590,227 A | 12/1996 | Osaka et al. ................. 385/53 |
| 5,601,611 A | 2/1997 | Fayram et al. ................ 607/6 |
| 5,603,697 A | 2/1997 | Grundy et al. ........... 604/95.04 |
| 5,604,433 A | 2/1997 | Theus et al. ................ 324/251 |
| 5,611,016 A | 3/1997 | Fangmann et al. .......... 385/100 |
| 5,619,605 A | 4/1997 | Ueda et al. .................... 385/80 |
| 5,626,618 A | 5/1997 | Ward et al. ..................... 607/5 |
| 5,626,619 A | 5/1997 | Jacobson et al. ............... 607/5 |
| 5,631,988 A | 5/1997 | Swirhun et al. .............. 385/89 |
| 5,634,720 A | 6/1997 | Gallup et al. ............... 374/183 |
| 5,649,965 A | 7/1997 | Pons et al. ..................... 607/2 |
| 5,653,735 A | 8/1997 | Chen et al. .................... 607/9 |
| 5,654,317 A | 8/1997 | Fujioka et al. .............. 514/312 |
| 5,658,966 A | 8/1997 | Tsukamoto et al. .......... 522/99 |
| 5,679,026 A | 10/1997 | Fain et al. ................... 439/651 |
| 5,683,435 A | 11/1997 | Truex et al. ................. 607/37 |
| 5,697,958 A | 12/1997 | Paul et al. ................... 607/31 |
| 5,699,801 A | 12/1997 | Atalar et al. ................ 600/410 |
| 5,709,225 A | 1/1998 | Budgifvars et al. ......... 128/899 |
| 5,716,386 A | 2/1998 | Ward et al. ................. 607/106 |
| 5,723,856 A | 3/1998 | Yao et al. ............... 250/227.11 |
| 5,733,247 A | 3/1998 | Fallon ......................... 600/410 |
| 5,738,105 A | 4/1998 | Kroll .......................... 600/510 |
| 5,749,910 A | 5/1998 | Brumwell et al. ............ 607/36 |
| 5,752,977 A | 5/1998 | Grevious et al. ............. 607/32 |
| 5,755,739 A | 5/1998 | Sun et al. .................... 607/14 |
| 5,755,742 A | 5/1998 | Schuelke et al. ............. 607/27 |
| 5,759,197 A | 6/1998 | Sawchuk et al. ............. 607/36 |
| 5,761,354 A | 6/1998 | Kuwano et al. .............. 385/33 |
| 5,766,227 A | 6/1998 | Nappholz et al. .............. 607/9 |
| 5,766,527 A | 6/1998 | Schildgen et al. .......... 264/104 |
| 5,772,604 A | 6/1998 | Langberg et al. ........... 600/518 |
| 5,774,501 A | 6/1998 | Halpern et al. .............. 375/279 |
| 5,776,167 A | 7/1998 | Levine et al. .................. 607/9 |
| 5,776,168 A | 7/1998 | Gunderson .................. 607/27 |
| 5,782,241 A | 7/1998 | Felblinger et al. .......... 600/509 |
| 5,782,880 A | 7/1998 | Lahtinen et al. ............... 607/9 |
| 5,808,730 A | 9/1998 | Danielian et al. .......... 356/73.1 |
| 5,814,087 A | 9/1998 | Renirie ....................... 607/21 |
| 5,814,089 A | 9/1998 | Stokes et al. ................ 607/32 |
| 5,814,090 A | 9/1998 | Latterell et al. .............. 607/36 |
| 5,814,091 A | 9/1998 | Dahlberg et al. ............. 607/36 |
| 5,817,130 A | 10/1998 | Cox et al. ...................... 607/5 |
| 5,817,133 A | 10/1998 | Houben ......................... 607/9 |
| 5,817,136 A | 10/1998 | Nappholz et al. ............. 607/17 |
| 5,818,990 A | 10/1998 | Steijer et al. ................. 385/49 |
| 5,827,195 A | 10/1998 | Lander ....................... 600/509 |
| 5,827,997 A | 10/1998 | Chung et al. .......... 174/35 MS |
| 5,830,209 A | 11/1998 | Savage et al. ................ 606/15 |
| 5,836,895 A | 11/1998 | Ramsey, III ................ 600/593 |
| 5,861,012 A | 1/1999 | Stroebel ...................... 607/28 |
| 5,865,839 A | 2/1999 | Doorish ..................... 623/6.63 |
| 5,867,361 A | 2/1999 | Wolf et al. .................. 361/302 |
| 5,868,664 A | 2/1999 | Speier et al. ................ 600/112 |
| 5,869,412 A | 2/1999 | Yenni, Jr. et al. ........... 442/376 |
| 5,870,272 A | 2/1999 | Seifried et al. .............. 361/302 |
| 5,871,509 A | 2/1999 | Noren ........................... 607/9 |
| 5,871,512 A | 2/1999 | Hemming et al. ............ 607/28 |
| 5,873,898 A | 2/1999 | Hemming et al. ............ 607/28 |
| 5,882,108 A | 3/1999 | Fraizer ....................... 326/293 |
| 5,882,305 A | 3/1999 | Dumoulin et al. .......... 600/421 |
| 5,891,171 A | 4/1999 | Wickham ...................... 607/4 |
| 5,895,980 A | 4/1999 | Thompson ................... 607/36 |
| 5,897,577 A | 4/1999 | Cinbis et al. ................ 607/28 |
| 5,899,927 A | 5/1999 | Ecker et al. ................. 607/23 |
| 5,902,326 A | 5/1999 | Lessar et al. ................ 607/36 |
| 5,916,162 A | 6/1999 | Snelten et al. .............. 600/411 |
| 5,916,237 A | 6/1999 | Schu ............................ 607/2 |
| 5,917,625 A | 6/1999 | Ogusu et al. ................. 385/24 |
| 5,919,135 A | 7/1999 | Lemelson ................... 600/407 |
| 5,928,145 A | 7/1999 | Ocali et al. ................. 600/410 |
| 5,928,270 A | 7/1999 | Ramsey, III ................... 607/5 |
| 5,928,570 A | 7/1999 | Reo ........................... 252/514 |
| 5,940,554 A | 8/1999 | Chang et al. ................ 385/22 |
| 5,946,086 A | 8/1999 | Bruce ...................... 356/243.8 |
| 5,951,596 A | 9/1999 | Bellinger .................... 607/89 |
| 5,954,660 A | 9/1999 | Legay et al. ................ 600/509 |
| 5,957,857 A | 9/1999 | Hartley ....................... 600/521 |

| Patent | Date | Inventor | Class |
|---|---|---|---|
| 5,963,034 A | 10/1999 | Mahapatra et al. | 324/244.1 |
| 5,963,690 A | 10/1999 | Cheng | 385/76 |
| 5,967,977 A | 10/1999 | Mullis et al. | 600/380 |
| 5,968,083 A | 10/1999 | Ciciarelli et al. | 607/62 |
| 5,973,779 A | 10/1999 | Ansari et al. | 356/301 |
| 5,973,906 A | 10/1999 | Stevenson et al. | 361/302 |
| 5,978,710 A | 11/1999 | Prutchi et al. | 607/17 |
| 5,982,961 A | 11/1999 | Pan et al. | 385/30 |
| 5,985,129 A | 11/1999 | Gough et al. | 205/724 |
| 5,987,995 A | 11/1999 | Sawatari et al. | 73/705 |
| 5,999,853 A | 12/1999 | Stoop et al. | 607/9 |
| 5,999,857 A | 12/1999 | Weijand et al. | 607/60 |
| 6,005,191 A | 12/1999 | Tzeng et al. | 174/102 R |
| 6,011,994 A | 1/2000 | Kronberg | 607/66 |
| 6,013,376 A | 1/2000 | Yenni, Jr. | 428/458 |
| 6,016,448 A | 1/2000 | Busacker et al. | 607/29 |
| 6,016,477 A | 1/2000 | Ehnebuske et al. | 705/7 |
| 6,023,641 A | 2/2000 | Thompson | 607/9 |
| 6,024,738 A | 2/2000 | Daikuzono et al. | 606/7 |
| 6,026,316 A | 2/2000 | Kucharczyk | 600/420 |
| 6,029,086 A | 2/2000 | Kim et al. | 607/9 |
| 6,029,087 A | 2/2000 | Wohlgemuth | 607/9 |
| 6,031,710 A | 2/2000 | Wolf et al. | 361/302 |
| 6,036,639 A | 3/2000 | Allred, III et al. | 600/193 |
| 6,036,654 A | 3/2000 | Quinn et al. | 600/526 |
| 6,044,301 A | 3/2000 | Hartlaub et al. | 607/31 |
| 6,052,613 A | 4/2000 | Takaki | 600/479 |
| 6,052,614 A | 4/2000 | Morris, Sr. et al. | 600/509 |
| 6,052,623 A | 4/2000 | Fenner et al. | 607/36 |
| 6,055,455 A | 4/2000 | O'Phelan et al. | 607/36 |
| 6,056,415 A | 5/2000 | Alled, III et al. | 362/202 |
| 6,056,721 A | 5/2000 | Shulze | 604/101.05 |
| 6,064,906 A | 5/2000 | Langberg et al. | 600/518 |
| 6,066,096 A | 5/2000 | Smith et al. | 600/439 |
| 6,067,472 A | 5/2000 | Vonk et al. | 607/128 |
| 6,076,003 A | 6/2000 | Rogel | 600/390 |
| 6,080,829 A | 6/2000 | Tapsak et al. | 528/35 |
| 6,090,473 A | 7/2000 | Yoshikawa et al. | 428/209 |
| 6,090,728 A | 7/2000 | Yenni, Jr. et al. | 442/117 |
| 6,091,015 A | 7/2000 | del Valle et al. | 136/243 |
| 6,091,744 A | 7/2000 | Sorin et al. | 372/20 |
| 6,091,987 A | 7/2000 | Thompson | 607/2 |
| 6,101,973 A | 8/2000 | Stewart et al. | 118/723 ER |
| 6,118,910 A | 9/2000 | Chang | 385/16 |
| 6,119,031 A | 9/2000 | Crowley | 600/407 |
| 6,129,745 A | 10/2000 | Sun et al. | 607/27 |
| 6,134,003 A | 10/2000 | Tearney et al. | 356/479 |
| 6,134,478 A | 10/2000 | Spehr | 607/115 |
| 6,142,678 A | 11/2000 | Cheng | 385/79 |
| 6,144,205 A | 11/2000 | Souza et al. | 324/322 |
| 6,144,866 A | 11/2000 | Miesel et al. | 600/333 |
| 6,144,881 A | 11/2000 | Hemming et al. | 607/28 |
| 6,146,415 A | 11/2000 | Fitz | 623/1.11 |
| 6,148,222 A | 11/2000 | Ramsey, III | 600/380 |
| 6,148,229 A | 11/2000 | Morris, Sr. et al. | 600/509 |
| 6,149,313 A | 11/2000 | Giebel et al. | 385/59 |
| 6,163,724 A | 12/2000 | Hemming et al. | 607/28 |
| 6,166,806 A | 12/2000 | Tjin | 356/336 |
| 6,169,921 B1 | 1/2001 | Knight et al. | 607/4 |
| 6,171,240 B1 | 1/2001 | Young et al. | 600/410 |
| 6,173,203 B1 | 1/2001 | Barkley et al. | 607/5 |
| 6,179,482 B1 | 1/2001 | Takizawa et al. | 385/81 |
| 6,188,926 B1 | 2/2001 | Vock | 607/9 |
| 6,192,261 B1 | 2/2001 | Gratton et al. | 600/310 |
| 6,198,968 B1 | 3/2001 | Prutchi et al. | 607/9 |
| 6,198,972 B1 | 3/2001 | Hartlaub et al. | 607/63 |
| 6,208,899 B1 | 3/2001 | Kroll | 607/9 |
| 6,216,041 B1 | 4/2001 | Tierney et al. | 607/101 |
| 6,223,083 B1 | 4/2001 | Rosar | 607/60 |
| 6,226,545 B1 | 5/2001 | Gilderdale | 600/423 |
| 6,230,060 B1 | 5/2001 | Mawhinney | 607/101 |
| 6,236,879 B1 | 5/2001 | Konings | 600/424 |
| 6,238,686 B1 | 5/2001 | Burrell et al. | 424/423 |
| 6,240,317 B1 | 5/2001 | Villaseca et al. | 607/60 |
| 6,245,020 B1 | 6/2001 | Moore et al. | 600/466 |
| 6,246,910 B1 | 6/2001 | Bonnet et al. | 607/18 |
| 6,247,474 B1 | 6/2001 | Greeninger et al. | 128/899 |
| 6,254,632 B1 | 7/2001 | Wu et al. | 623/1.15 |
| 6,256,537 B1 | 7/2001 | Stoop et al. | 607/14 |
| 6,256,541 B1 | 7/2001 | Heil et al. | 607/123 |
| 6,258,087 B1 | 7/2001 | Edwards et al. | 606/41 |
| 6,259,843 B1 | 7/2001 | Kondo | 385/104 |
| 6,259,954 B1 | 7/2001 | Conger et al. | 607/122 |
| 6,263,229 B1 | 7/2001 | Atalar et al. | 600/423 |
| 6,263,242 B1 | 7/2001 | Mika et al. | 607/9 |
| 6,266,555 B1 | 7/2001 | Werner et al. | 600/523 |
| 6,266,563 B1 | 7/2001 | Knight et al. | 607/5 |
| 6,266,564 B1 | 7/2001 | Hill et al. | 607/9 |
| 6,266,566 B1 | 7/2001 | Nichols et al. | 607/30 |
| 6,270,457 B1 | 8/2001 | Bardy | 600/300 |
| 6,270,831 B2 | 8/2001 | Kumar et al. | 427/224 |
| 6,272,377 B1 | 8/2001 | Sweeney et al. | 600/515 |
| 6,272,380 B1 | 8/2001 | Warman et al. | 607/5 |
| 6,274,265 B1 | 8/2001 | Kraska et al. | 429/90 |
| 6,275,730 B1 | 8/2001 | Knight et al. | 607/5 |
| 6,275,732 B1 | 8/2001 | Hsu et al. | 607/14 |
| 6,275,734 B1 | 8/2001 | McClure et al. | 607/27 |
| 6,277,078 B1 | 8/2001 | Porat et al. | 600/486 |
| 6,277,107 B1 | 8/2001 | Lurie et al. | 604/528 |
| 6,278,057 B1 | 8/2001 | Avellanet | 174/36 |
| 6,278,277 B1 | 8/2001 | Zeiger | 324/322 |
| 6,278,894 B1 | 8/2001 | Salo et al. | 600/547 |
| 6,278,897 B1 | 8/2001 | Rutten et al. | 607/122 |
| 6,296,654 B1 | 10/2001 | Ward | 606/192 |
| 6,317,633 B1 | 11/2001 | Jorgenson et al. | 607/28 |
| 6,367,984 B1 | 4/2002 | Stephenson et al. | 385/53 |
| 6,571,130 B1 * | 5/2003 | Ljungstrom et al. | 607/116 |

OTHER PUBLICATIONS

Carlton F. Roos, B.A. and Frank E. Carroll, Jr. M.D..; Fiber-Optic Pressure Transducer for Use Near MR Maganetic Fields; RSNA 1985; one page.

Kenneth A. Wickersheim and Mei H. Sun; Fiberoptic Thermotmetry and its Applications; J. Microwave Power 1987; pp. 85-94.

Anastazia Jerewski et al.; Development of an MRI-Compatible Catheter for Pacing the Heart: Initial In Vitro and In Vivo Results; ISMRM-1996; pp. 948-949.

Mark B. M. Hofman, Ph.D.; MRI-Compatible Cardiac Pacing Catheter; JMRI May/Jun. 1997; p. 612.

A. A. Damji et al.; RF Interference Suppression in a Cardiac Synchronization System Operating in a High Magnetic Field NMR Imaging System; Magnetic Resonance Imagan, vol. 6, pp. 637-640, 1988.

Frank G. Shellock, Ph.D. et al.; Burns Associated wit the use of Monitoring equipment during MR procedures; JMRI Jan./Feb. 1996; pp. 271-272.

J.A. Nyenhuis et al.; Heating near Implanted Medical Devices by the MRI RF-magnetic Field; IEEE Trans. Mag. Sept. 1999; four pages.

Frank G. Shellock, Ph.D.; eta l.; Cardiovascular Catheters and Accessories: Ex Vivo Testing of Ferromagnetism, Heating, and Artifacts Associated with MRI; JMRI Nov./Dec. 1998 vol. 8 #6; pp. 1338-1342.

J. Rod Gimbel et al.; Safe Performance of Magnetic Resonance; PACE, vol. 19 Jun. 1996; pp. 913-919.

National Library of Medicine; Pub Med; Pacing Clin Electrophysiol Jun. 1998; 21(6): 1336-9; Rapid Ventricular pacing in a pacemaker patient undergoing magnetic resonance imaging; p. 1.

National Library of Medicine; Pub Med; Am Heart J 1997 Set; 134(3):467-73; Effects of magnetic resonance imaging on cardiac pacemakers and electrodes; pp. 1-2.

M. Kusumoto et al., "Cardiac Pacing for the Clinician," Lippincott Williams & Wilkins; (2001); Chapter 1, pp. 9, 12, 13, 18, 22, 24.

Donald Fink; "Electronic Engineering," Electronic Engineers Handbook; 2nd edition, Mcgraw Hill; (1982); Section 14; pp. 29-45.

X Luo et al, "Electromagnetic Interference Shielding Using Continuous Carbon-Fiber Carbon-Matrix and Polymer-Matrix Composites," Composites Part B; Engineering; (1999); pp. 227-231.

D.D.L Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p 161-163.

M. Konings et al., "Catheters and Guidewires in Inerventional MRI; Problems and Solutions," Medical Mundi; 45/1; Mar. (2001).

M. Konings; "Development of an MR-Safe Tracking Catheter with a Laser Driven Tip Coil,".

EY Wong et al., "An Optical System for Wireless Detuning of Parallel Resonant Circuits" Journal of Magnetic Resonance Imaging; (2000); vol. 12, pp. 632-638.

Bernd Nowak; "Taking Advantage of Sophisticated Pacemaker Diagnostics," Excerpta Medica; (1999): pages 172D-179D.

Jose A. Jogler et al., "Interaction of a Commercial Heart Rate Monitor With Implanted Pacemakers," Excerpta Medica; (1999); pp. 790-792.

J.A. Pomposo et al., "Polypyrrole-based Conducting Hot Melt Adhesives for EMI Shielding Applications," Elsevier; Synthetic Metals 104; (1999); pp. 107-111.

K. Grattan et al., "Fiber Optic Sensor Technology: An Overview," Elsevier; Sensors and Actuators 82; (2000): pp. 40-61.

L. Rippert et al., "Optical and Acoustic Damage Detection in Laminated CFRP Composite Materials," Elsevier; Composites Science and Technology 60; (2000); pp. 2713-2724.

C. Strandman et al., "A Production Process of Silicon Sensor Elements for a Fibre-Optic Pressure Sensor," Elsevier; Sensors and Actuators A63; (1997); pp. 69-74.

D. Howard et al., "A Single-Fringe Etalon Silicon Pressure Transducer," Elsevier; Sensors and Actuators 86; (2000); pp. 21-25.

Dan Haronian, "Displacement Sensing Using Geometrical Modulation in Reflection Mode (GM-RM) of Coupled Optical Waveguides," J. Micromech, Microeng., (UK), (1998); pp. 323-326.

H Ghafouri-Shiraz, "A Novel Distributed Feedback Laser Diode Structure foran Optical Wavelength Tunable Filter," Semicond. Sci. Technol. 12; (UK), (1997); pp. 1161-1165.

L. Kasarian, "A New Optical Fiber Multiplexer for Distortion-Free Light Transfer im Multichannel Fiber Optic Sensor Systems,"Elsevier; Sensors and Actuators 84; (2000); pp. 250-258.

X. Yan et al., "Electric Field Controlled 2×2 Bypass Exchange Photorefractive Switch," IOP Publishing; (UK) (1998), pp. 383-386.

E. Piener et al., "A Micromachined Vibration Sensor Based on the Control of Power Transmitted Between Optical Fibres," Elsevier; Sensors and Actuators A65; (1998) pages 23-29.

D. Sun et al., "High Performance Unidirectional Electrooptic Modulator Based On Polymetric Highly Multi-Mode Waveguides, " Elsevier; Optics & Laser Technology 30; (1998); 481-489.

Engin Molva; "Microchip Lasers and Their Applications in Optical Microsystems," Elsevier; Optical Materials 11; (1999); pp. 289-299.

J. Linares et al., "Theory and Design of an Integrated Optical Sensor Based on Planar Waveguiding Lenses," Elsevier; Optics Communications 180; (2000); pp. 29-36.

O. Parriaux et al., "Coupling Gratings as Waveguide Functional Elements," IOP Publishing; Pure Appl. Opt. 5; (1996); pp. 453-469.

E T Enikov et al., "Three-Dimensional Microfabrication for a Multi- Degree of Freedom Capacitive Force Sensor Using Fibre-Chip Coupling" IOP Publishing; (UK); J. Micromechl. Microeng. 10;(2000) pp. 492-497.

J. Holm et al., "Through-Etched Silicon Carriers for Passive Alighnment of Optical Fibers to Surface-Active Optoelectronic Components" Elsevier;Sensors and Actuators 82; (2000) pp. 245-248.

M. Kimura et al., "Vibration Sensor Using Optical-Fiber Catilever with Bulb-Lens" Elsevier; Sensors and Actuators A66; (2000) pp. 178-183.

Y. Mao et al., "Three-Stage Wavelength Converter Based on Cross-Grain Modulation in Semiconductor Optical Amplifiers"Elsevier; Optics Communications 167; (1999) pp. 57-66.

X. Hu et al., "Dynamically Induced Irreversibility: Light Amplification and Quantum Noise Reduction in a V-Type Three-Level System" IOP Publishing; J. Opt. B: Quantum Semiclass. Opt. 2; (UK) (2000); pp. 570-575.

Y. Yim et al., "Lithium Niobate Integrated-Optic Voltage Sensorwith Variable Sensing Ranges" Elsevier; Optics Communications 152; Jul. 1, 1998; pp. 225-228.

C. Lee et al., "Electromagnetic Interference Shilding Efficiency of Polyaniline Mixtures and Multilayer Films" Elsevier; Synthetic Metals 102; (1999) pages 1346-1349.

Marc Desmulliez, "Optoelectronics-VLSI System Integration Technological Challenges" Elsevier; Materials Science and Engineering B74; (2000) pp. 269-275.

J. Zook et al., "Fiber-optic Vibration Sensor Baed on Frequency Modulation of Light-Excited Oscillators"Elsevier; Sensors and Actuators 83; (2000); pp. 270-276.

M. Reta-Hernandez et al., "Attenuation of Low Frequency Magnetic Fields Using Active Shielding" Elsevier; Electric Power Systems Research 45; (1998); pp. 57-63.

C. Huang et al., "The EMI Shielding Effectiveness of PC/ABS/Nickel-Coated Carbon-Fibre Composites" Elsevier; European Polymer Journal 36; (2000) pp. 2727-2737.

M. Balucani et al., "Optical Link for DigitalTransmissions Using Porou Silicon Light Emitting Diode" Elsevier; Journal of Non-Crystalline Solids 266-269; (2000) pp. 1238-1240.

D. Egelman et al., "Calcium Dynamics in the Extracellular Space of Mammalian Nerual Tissue" Biophysical Journal; vol. 76; Apr. 1999; pp. 1856-1867.

M. Reta-Hernandez et al., "Attenutation of low frequency magnetic fields using active shielding" Elsevier; European Polymer Journal 36; (2000) pp. 1238-1240.

* cited by examiner

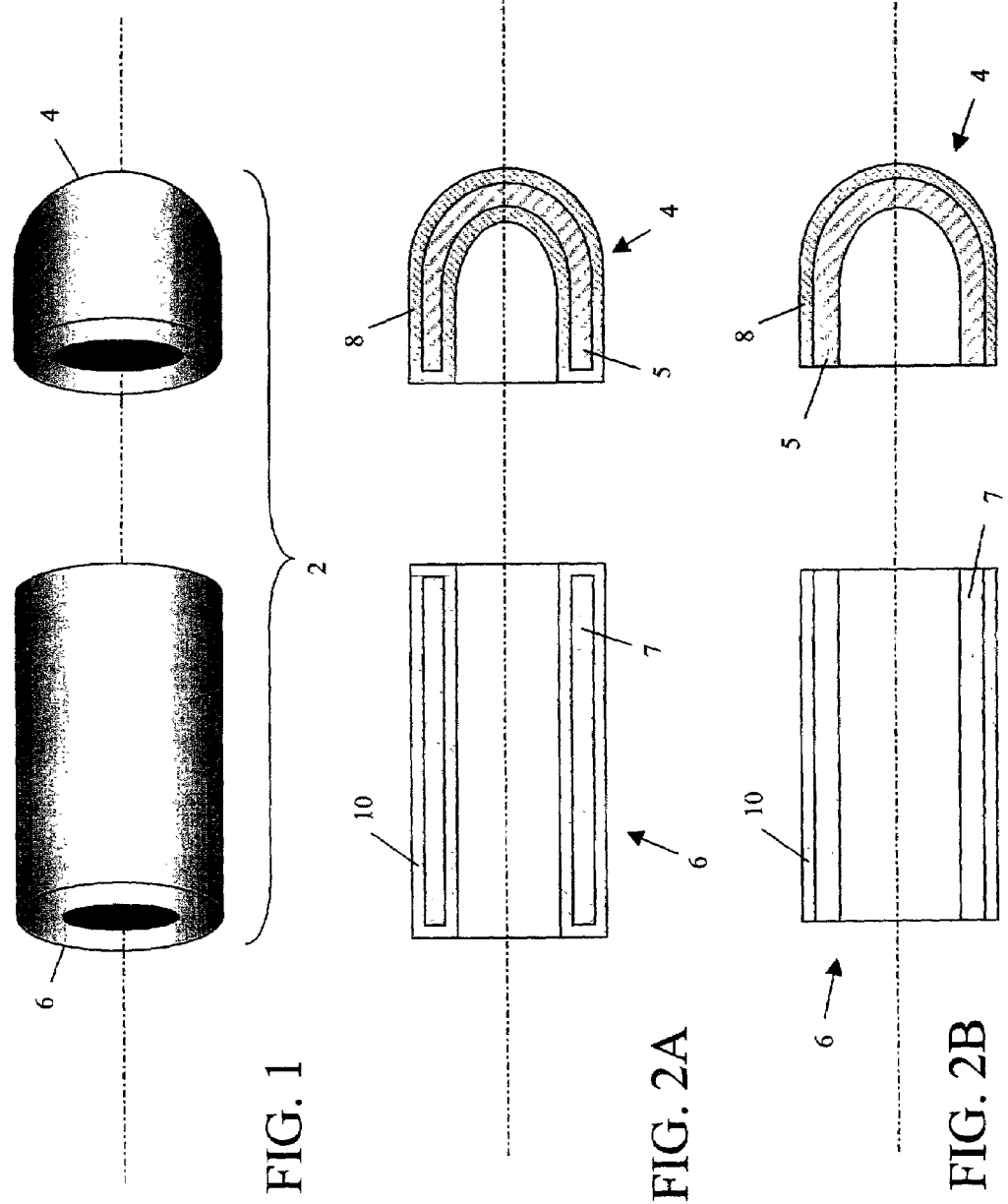

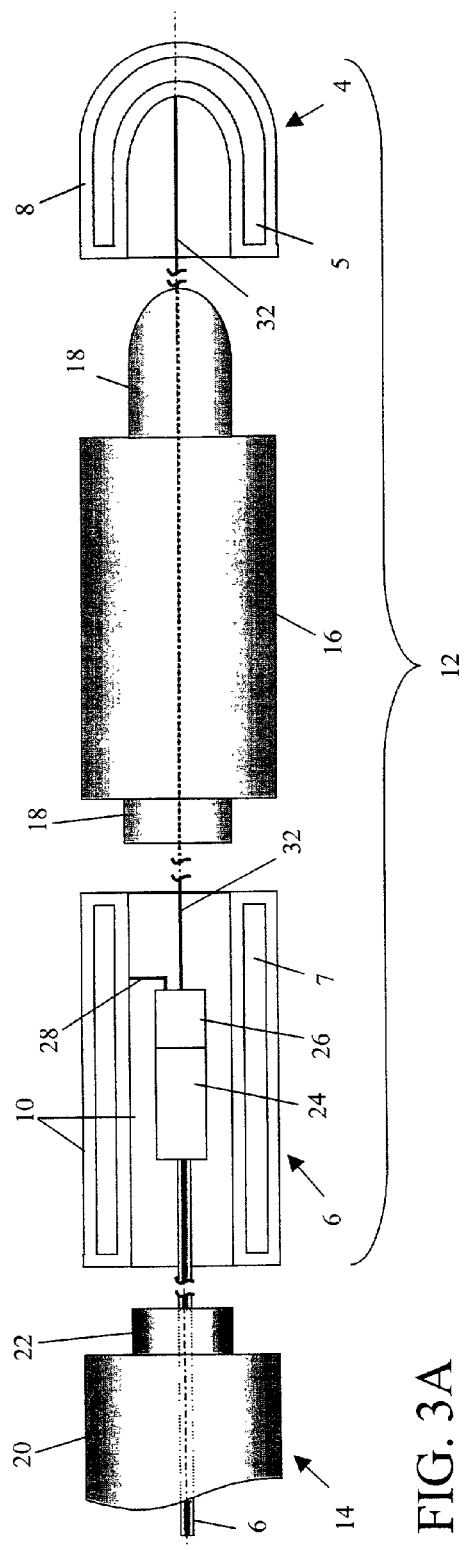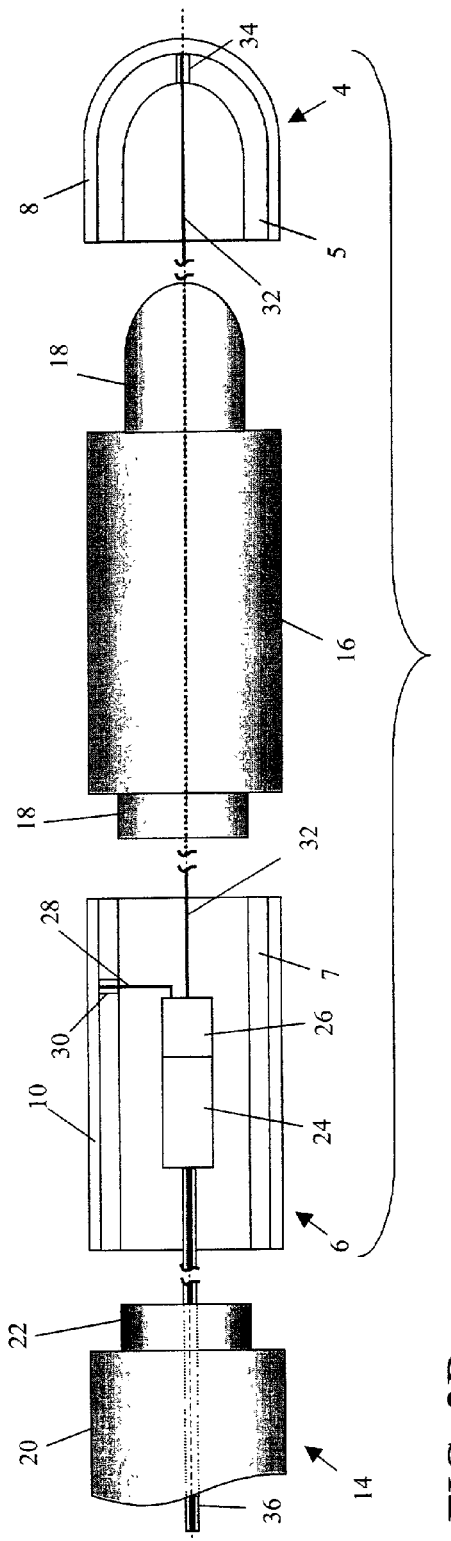
FIG. 3A
FIG. 3B

CERAMIC CARDIAC ELECTRODES

BACKGROUND OF THE INVENTION

1. Field of the Invention

The present invention relates to pacemakers. More particularly, the invention concerns cardiac electrodes for use with pacemakers, and especially pacemakers designed to be compatible with MRI diagnostic apparatus.

2. Description of Prior Art

The metallic cardiac electrodes and leads used in conventional cardiac stimulation and monitoring devices have always been a problem. They tend to fatigue, corrode, and break. Their physical properties (corrosion, strength, chemical activity, etc.) limit the materials which can be used to titanium, platinum metals, their alloys, to certain stainless steels, and to special structures to limit fatigue (such as spring coils, metal cladding, multiple strands, etc.) With respect to metallic leads, a leaky interface is often produced between the metal and the insulating sheath that surrounds the leads.

The problem of metallic leads has been addressed by applicant's assignee in an effort to provide a pacemaker that is compatible with MRI diagnostic imaging procedures. See copending Ser. Nos. 09/864,944 and 09,865,049, both filed on May 24, 2001, and copending Ser. Nos. 09/885,867 and 09/885,868, both filed on Jun. 20, 2001. In these copending patent applications, the contents of which are fully incorporated herein by this reference, MRI compatible/safe pacemakers are disclosed for both implantable and wearable use. The disclosed pacemakers feature photonic catheters carrying optical signals in lieu of metallic leads carrying electrical signals in order to avoid the dangers associated with MRI-generated electromagnetic fields.

The devices of the copending applications also use only non-ferromagnetic materials and attempt to minimize the number of metal components of any kind. In accordance with these goals, the copending applications propose electrodes that are made from non-ferromagnetic metals such as titanium, platinum, and platinum-containing alloys. In addition, the copending applications advise that non-metals may also be used to provide the electrodes. It is the purpose and goal of the present invention to address such non-metallic electrodes and to propose specific nonmetallic electrode constructions that could be used to advantage in an MRI compatible/safe pacemaker, as well as in pacemakers and other electrical stimulation devices that are not necessarily designed for MRI compatibility and safety.

SUMMARY OF THE INVENTION

The foregoing problems are solved and an advance in the art is provided by an electrode termination pair of novel construction for the distal end of a pacemaker catheter, and particularly a photonic pacemaker catheter. The electrode termination pair includes tip and ring structures that are made from a body-compatible ceramic material that is thinly coated, by electroplating, sputtering or other deposition technique, etc., with a suitable electrode metal such as platinum, titanium, or alloys thereof. The tip and ring structures may be formed on separate ceramic base structures or they may be integrated on a single ceramic base structure. If separate structures are used, the tip and ring can be separated by a short insulating stub structure having the same external diameter as the tip and ring. The stub structure can be made of silicone rubber, polyethylene, urethane, or some other material having suitable insulating properties and which is compatible with the human body. The ring structure is electrically connected to the positive electrical pulse output of the pacemaker, and the tip structure is electrically connected to the negative pulse output of the pacemaker. If the electrode termination pair is incorporated in a photonic pacemaker, the ring or the tip can be adapted to house an optical termination and an opto-electric transducer for stimulation pulse delivery to implanted cardiac tissue. The ring or the tip may also house an R-wave amplifier and an electro-optical transducer for pulse monitoring of implanted cardiac tissue. Additional functionality, such as a partial oxygen monitor, may also be provided.

Accordingly, it is a principal object of the invention is to provide "tip and ring" electrode system with no magnetic materials and very little metallic content of any kind.

A further object of the invention is to provide an electrode system for delivering stimulation impulses into cardiac tissue without adverse effect from MRI induced electromagnetic fields, and in a way that will not will not appreciably affect the accuracy of an MRI diagnostic record.

A further object of the invention is to provide an enclosure for an opto-electrical transducer that converts light pulses from a photonic catheter into stimulating electrical impulses to drive the heart.

BRIEF DESCRIPTION OF THE DRAWINGS

The foregoing and other features and advantages of the invention will be apparent from the following more particular description of preferred embodiments of the invention, as illustrated in the accompanying Drawing in which:

FIG. 1 is an exploded perspective view of an electrode termination pair constructed in accordance with a preferred embodiment of the present invention;

FIGS. 2A and 2B are sectional views taken along the axial centerline of alternative electrode termination pairs constructed in accordance with the embodiment of FIG. 1.

FIGS. 3A and 3B are exploded partial sectional views showing alternative electrode termination pairs constructed in accordance with the embodiment of FIG. 1 and mounted to the end of a photonic catheter and housing an opto-electrical transducer therein;

DETAILED DESCRIPTION OF PREFERRED EMBODIMENTS

Figure 4A:
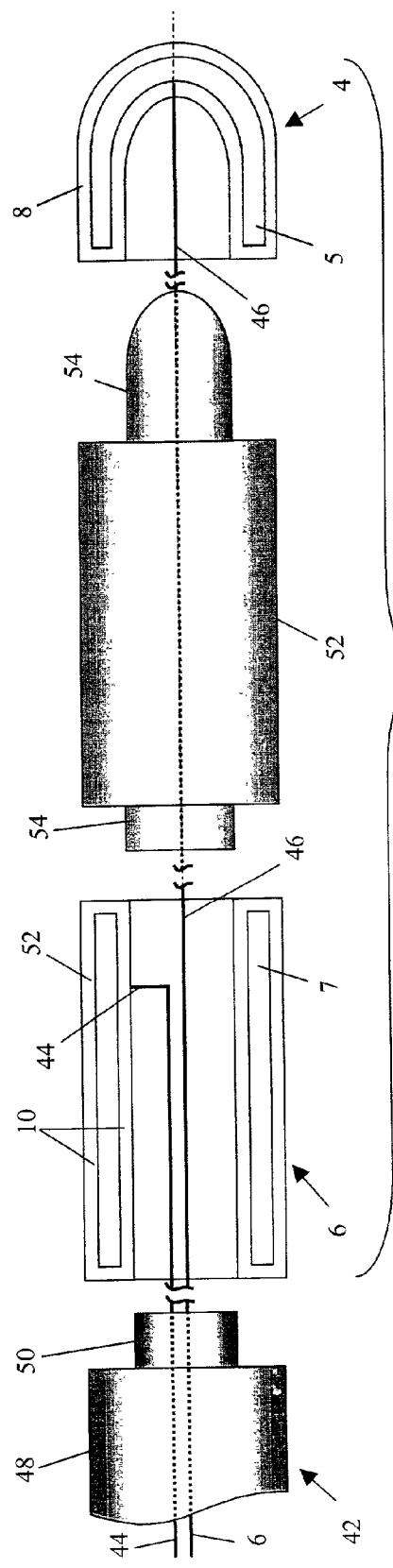
FIGS. 4A and 4B are exploded partial sectional views showing alternative electrode termination pairs constructed in accordance with the embodiment of FIG. 1 and mounted to the end of a metallic lead catheter.

Turning now to FIG. 1, a preferred embodiment of the invention is shown in the form of a electrode termination pair 2. The electrode termination pair 2 includes a ceramic cup (tip) 4 and a ceramic ring 6. The tip 4 and the ring 6 are both substantially cylindrical in shape, and preferably have the same wall thickness. Note that the tip 4 has a rounded nose portion and a base portion that is planar. The ring 6 has proximal and distal end portions that are both preferably planar.

As shown in FIGS. 2A and 2B, the tip 4 includes a ceramic base structure 5 and an electrically conductive coating 8. The ring 6 includes a ceramic base structure 7 and an electrically conductive coating 10. The difference between FIGS. 2A and 2B is that all exposed surfaces of the ceramic base structures 5 and 7 are coated in FIG. 2A, whereas only the outer surface of the ceramic base structures 5 and 7 are coated in FIG. 2B.

The material used to form the ceramic base structures 5 and 7 is preferably a suitable bio-compatible ceramic material such a ceramic of the type commonly used for joint prostheses. By way of example only, such material is available from Ceramic Components Inc. of Latrobe, Pa. To form the ceramic base structures 5 and 7, a ceramic slurry is formed into the desired shapes and fired to bake the ceramic material.

The electrically conductive coatings 8 and 10 are preferably formed by very thinly coating the ceramic base structures 5 and 7, as by electroplating, sputtering or other deposition technique, etc., with a suitable metal. If MRI compatibility is desired, the metal preferably has low magnetic susceptibility, such as titanium, platinum, or alloys thereof. Preferably, if MRI compatibility is desired, the coatings 8 and 10 are applied as thin as possible to achieve the twin goals of efficient electrical interaction with an implanted heart while minimizing interaction with MRI induced electromagnetic fields. By way of example, the thickness of the coatings 8 and 10 may range from monomolecular thickness to sub-micron or micron level thickness. An adhesion promoting sublayer (not shown) may be applied to the ceramic base structures 5 and 7 prior to application of the foregoing coatings.

Turning now to FIGS. 3A and 3B, the electrode termination pair 2 of FIG. 1 may be configured in a tip/ring assembly 12 and mounted to the distal end of a photonic catheter 14 of the type disclosed in the copending applications referenced above. In FIG. 3A, the tip and ring structures 4 and 6 are coated on all surfaces with an electrically conductive coating. In FIG. 3B, only the outside surfaces of the tip 4 and ring 6 are coated.

The tip and ring assembly 12 includes the tip 4, the ring 6, and a short intermediate stub 16 that is solid, generally cylindrical in shape, and made from silicone, polyurethane, polyethylene or other suitable bio-compatible electrically insulating material. The outside diameter of the stub 16 preferably equals the outside diameter of the tip 4 and the ring 6 in order to facilitate efficient implantation and removal in a patient. As described in more detail below, the interior of the stub 16 carries a metallic lead element that extends between the tip 4 and the ring 6. The stub 16 includes a pair of end portions 18 that are preferably of reduced diameter so as to fit snugly inside the tip 4 and the ring 6 and thereby enhance connection integrity. The stub 16 can be implemented as a preformed element whose reduced diameter end portions 18 are respectively attached to the inside walls of the tip 4 and the ring 6 by way of bonding using a suitable medical adhesive. More preferably, however, the stub 16 is cast in place between the tip 4 and the ring 6 using a suitable bio-compatible material, such as silicone, polyurethane, polyethylene or the like. The reduced diameter end portions 18 would then be formed as a result of the stub material being forced into the respective interiors of the tip 4 and the ring 6 prior to hardening into a solid mass.

The photonic catheter 14 is a generally cylindrical element whose exterior sheath 20 is made from silicone, polyurethane, polyethylene or other suitable bio-compatible electrically insulating material. The outside diameter of the sheath 20 is preferably the same as that of the ring 6 in order to facilitate efficient implantation and removal in a patient. As described in more detail below, the interior of the sheath 20 carries one or more optical conductors (e.g., fiber optic elements) that extend to the ring 6 from a photonic pacemaker pulsing unit or other medical device (not shown). The sheath 20 includes a distal end portion 22 that is preferably of reduced diameter so as to fit snugly inside the ring 6 and thereby enhance connection integrity. Like the stub 16, the sheath 20 can be implemented as either a preformed element or can be cast in place. If the sheath 20 is a preformed element, its reduced diameter end portion 22 can be secured to the inside wall of the ring 6 by way of bonding using a suitable medical adhesive. If the sheath 20 is cast in place, the reduced diameter end portion 22 would be formed as a result of the sheath material being forced into the interior of the ring 6 prior to hardening into a solid mass An optical termination unit 24 is disposed within the ring 6 and is associated with an opto-electrical transducer 26 (described in more detail below). A positive electrical output of the opto-electrical transducer 26 connects to a short metallic lead 28 made from copper or other suitable electrically conductive material of low magnetic susceptance. The metallic lead 28 is electrically connected, as by soldering or the like, to the metallic coating 10 of the ring 6. Note that in FIG. 3B, a small hole 30 can be made in the ring 6 to facilitate electrical connection of the lead 28 to the metallic coating 10. Other connection schemes could also be employed. A negative electrical output of the opto-electrical transducer 26 connects to a longer metallic lead 32 that is also made from copper or other suitable electrically conductive material of low magnetic susceptance. The metallic lead 32 extends through the stub 16 (which is preferably molded around the lead 32 as indicated above) and is electrically connected, as by soldering or the like, to the metallic coating 8 of the tip 4. Note that in FIG. 3B a small hole 34 is made in the tip 4 to facilitate electrical connection of the lead 32 to the metallic coating 8. Again, alternative connection schemes could also be used.

The tip/ring assembly 12 must be small enough to be implantable in a human heart. A diameter of about 5 millimeters or less and an overall length of about 4 centimeters or less should suffice. When the tip/ring assembly 12 is so implanted, the tip 4 will typically be embedded in the endocardial tissue of the heart, while the ring 6 will be situated in one of the chambers of the heart, such as the right ventricle, such that the ring 6 is placed in electrical contact with the endocardium via the patient's ventricular (or atrial) blood. During pacemaker operation, an optical pulse emanating from a photonic pacemaker pulsing unit or other medical device (not shown) is sent down at least one fiber optic element 36 of the photonic catheter 14. The fiber optic element 36 passes into the interior of the ring 6 and is terminated at the optical termination unit 24. The fiber optic element 36 delivers the optical pulse to the opto-electrical transducer 26, which is preferably implemented as a photodiode array situated on or within the optical termination unit 24. The opto-electrical transducer 26 produces an electrical pulse that negatively drives the tip 4 with respect to the ring 6 at a potential of about 3–4 volts and a current level of about 3 milliamperes for a total power output of about 10 milliwatts. The metallic coatings 8 and 10 respectively formed on the tip 4 and the ring 6 will provide highly efficient electrical contact with the heart for delivering the pulse while minimizing the use of metallic material that might otherwise result in complications during MRI imaging. Note that a sensing function for monitoring the heart's "R" wave signals could be added by introducing an R-wave amplifier and an electro-optical transducer (not shown) into the interior of the ring 6 and making appropriate electrical connections to the tip 4 and the ring 6.

Figure 4B:
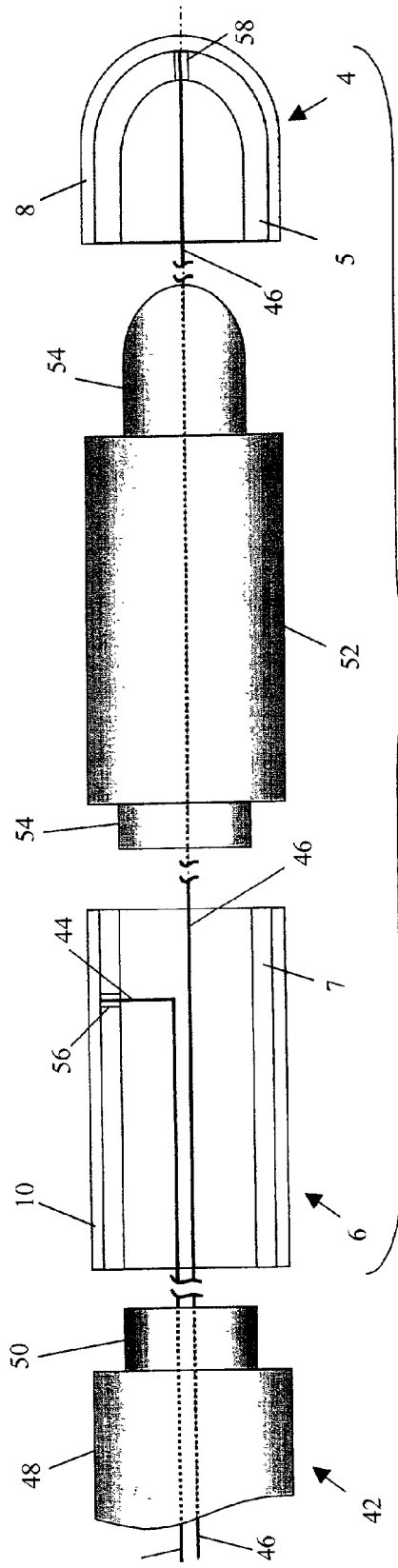

Turning now to FIGS. 4A and 4B, the electrode termination pair 2 of FIG. 1 is configured in a tip/ring assembly 40 that is mounted to the distal end of a conventional pacemaker catheter 42. In FIG. 4A, the ceramic base structures 5 and 7 of the tip 4 and the ring 6 are coated on all surfaces with respective electrically conductive coatings 8 and 10. In FIG. 4B, only the outside surfaces of the tip and ring base structures 5 and 7 are coated.

The catheter 42 comprises positive and negative metallic electrode leads 44 and 46, preferably made of MP35 alloy or non-magnetic stainless steel. The leads 44 and 46 are surrounded by a cylindrical sheath 48 made from silicone, polyurethane, polyethylene or other suitable bio-compatible material. The outside diameter of the sheath 48 is selected so as to match the outside diameter of the ring 6. A reduced diameter end portion 50 of the sheath 48 snugly engages the inside wall of the ring 6.

A stub 52 is used to interconnect the tip 4 and the ring 6. The stub 52 can be formed in the same manner as the stub 16 of FIGS. 3A and 3B. The outside diameter of the stub 52 is selected so as to match the outside diameter of the tip 4 and the ring 6. Reduced diameter end portions 54 of the stub 52 respectively engage the inside walls of the tip 4 and the ring 6.

The metallic leads 44 and 46 are respectively connected to the ring 6 and the tip 4. The positive lead 44 extends into the interior of the ring 6 and is electrically connected, as by soldering or the like, to the metallic coating 10. Note that in FIG. 4B, a small hole 56 can be made in the ring 6 to facilitate electrical connection of the lead 28 to the metallic coating 10. Other connection schemes could also be employed. The negative lead 46 extends through the ring 6 and the stub 52 (which is preferably molded around the lead 46 as indicated above) and is electrically connected, as by soldering or the like, to the metallic coating 8 of the tip 4. Note that in FIG. 4B a small hole 58 is made in the tip 4 to facilitate electrical connection of the lead 46 to the metallic coating 8. Again, alternative connection schemes could also be used.

Figure 5:
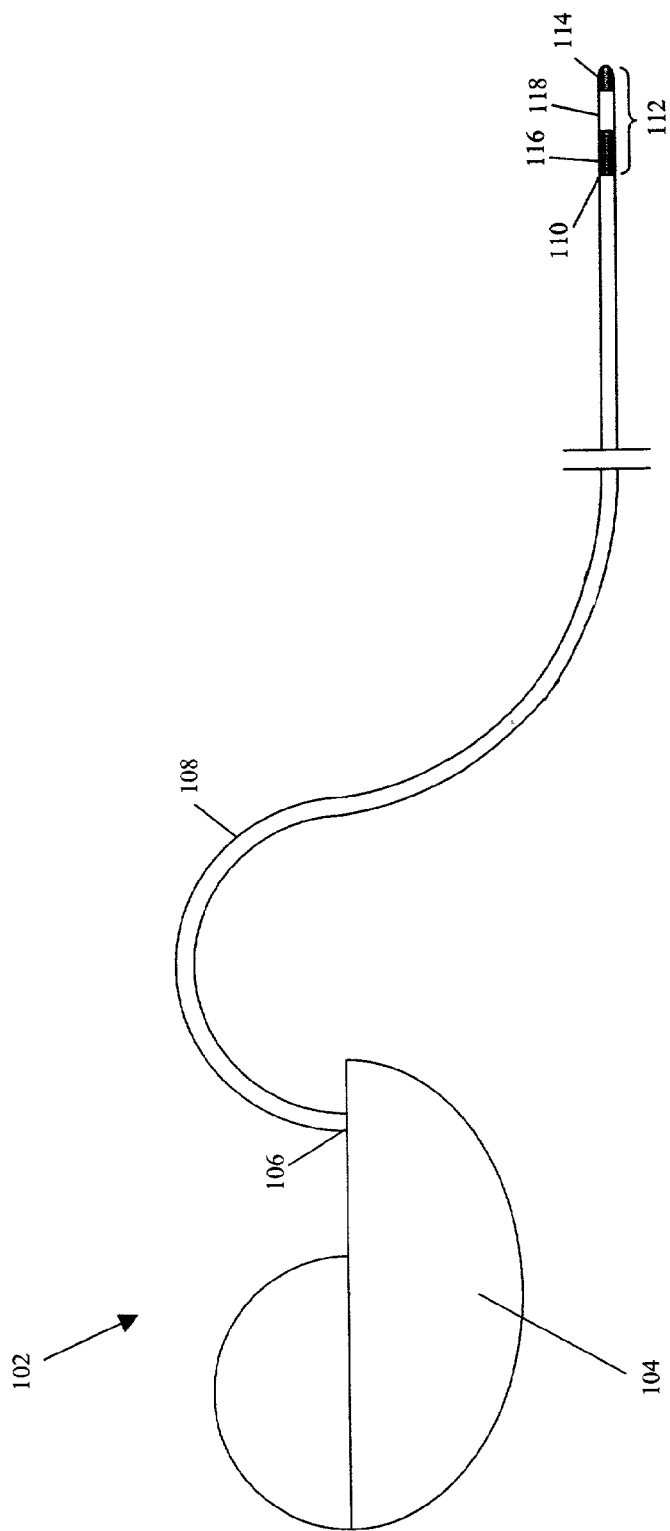
FIG. 5 is a diagrammatic view of an implantable pacemaker comprising an electrode termination pair in accordance with the invention.

Turning now to FIG. 5, an implantable pacemaker 102 is shown that may be constructed in accordance with the present invention. The pacemaker 102 includes a first (main) enclosure 104 that is connected to the proximal end 106 of a catheter 108, which may be photonic or non-photonic. A distal end 110 of the catheter 108 mounts an electrode termination pair 112 constructed in accordance with a suitable one of the embodiments disclosed herein. Thus, the electrode termination pair 112 includes a coated ceramic tip 114 and a coated ceramic ring 116 separated by a short insulative spacer 118.

Figure 6:
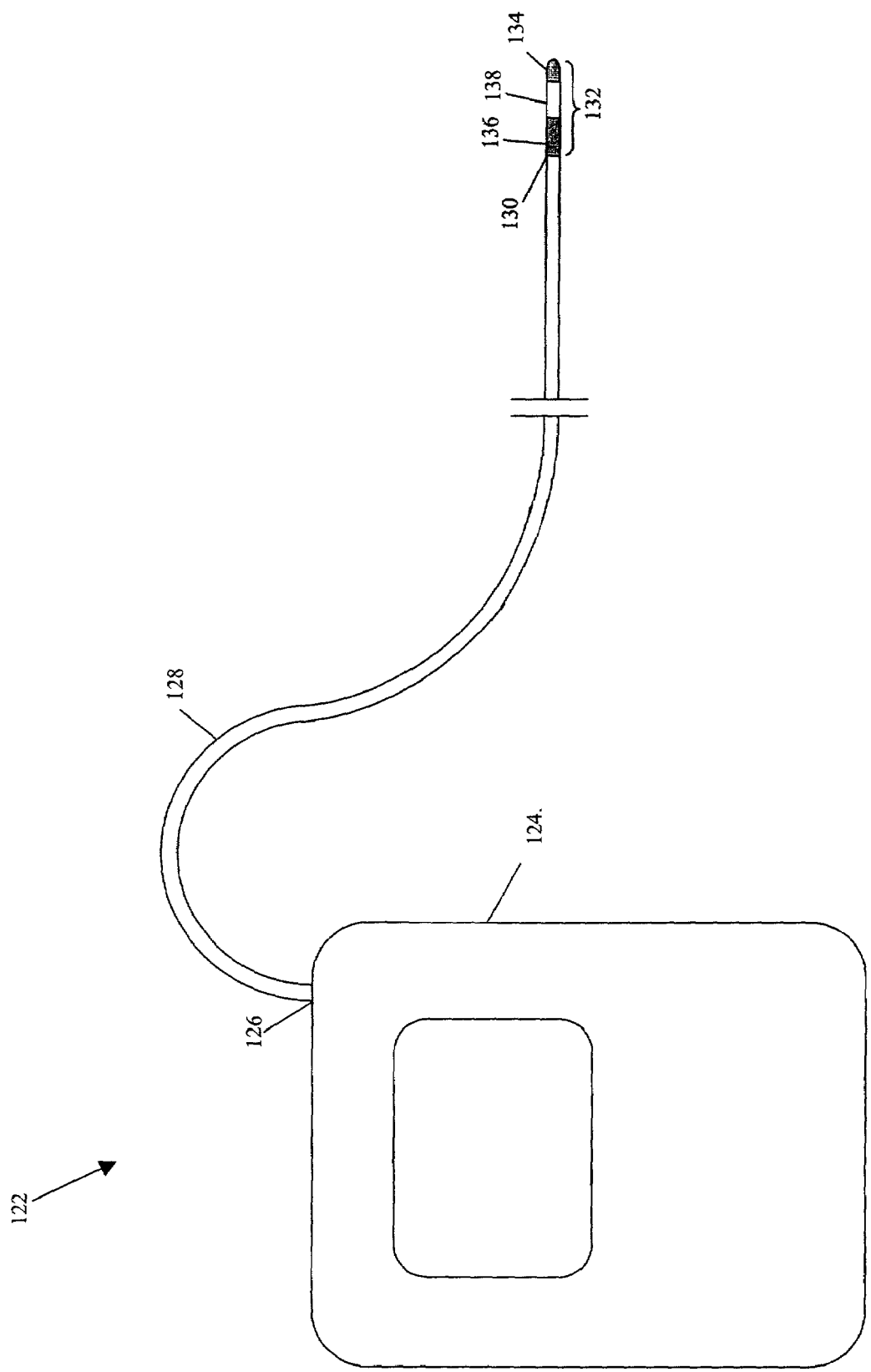
FIG. 6 is a diagrammatic view of a wearable pacemaker comprising an electrode termination pair in accordance with the invention.

Turning now to FIG. 6, a wearable pacemaker 122 is shown that may be constructed in accordance with the present invention. The pacemaker 122 includes a first (main) enclosure 124 that is connected to the proximal end 126 of a catheter 128, which may be photonic or non-photonic. A distal end 130 of the catheter 128 mounts an electrode termination pair 132 constructed in accordance with a suitable one of the embodiments disclosed herein. Thus, the electrode termination pair 132 includes a coated ceramic tip 134 and a coated ceramic ring 136 separated by a short insulative spacer 138.

Figure 7:
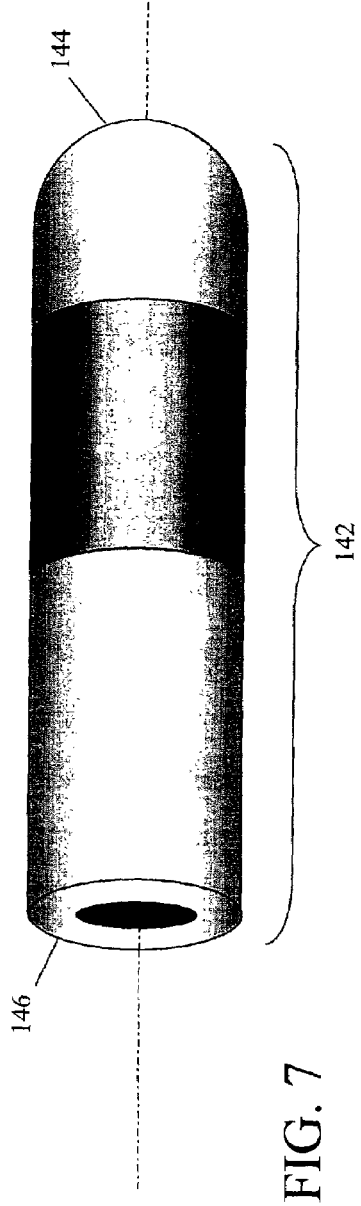
FIG. 7 is a perspective view of an electrode termination pair constructed in accordance with a preferred embodiment of the present invention.
Figure 8A:
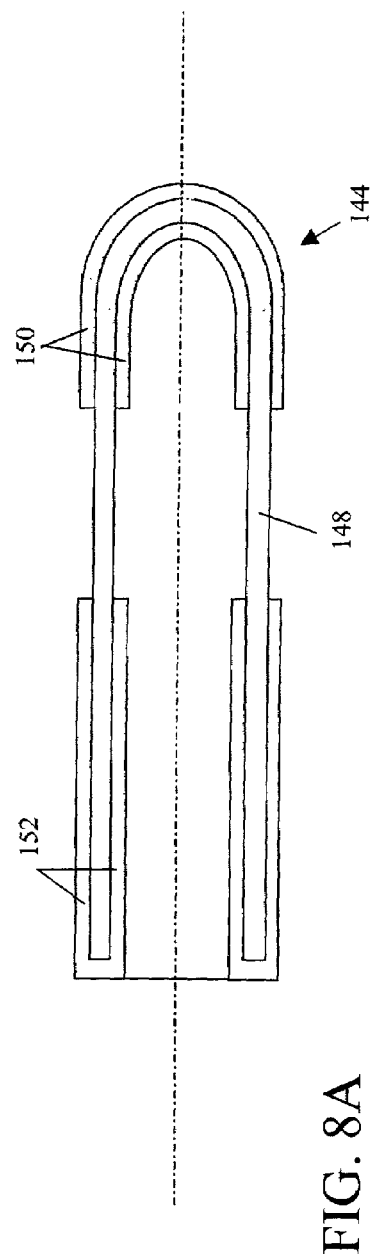
FIGS. 8A and 8B are sectional views taken along the axial centerline of alternative electrode termination pairs constructed in accordance with the embodiment of FIG. 7.
Figure 8B:
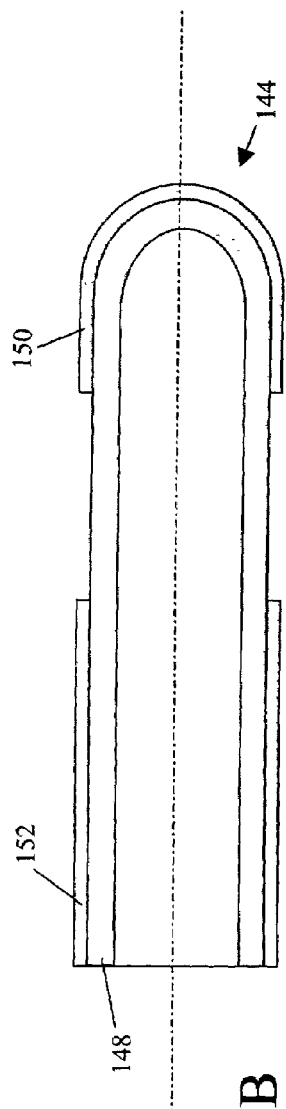

Turning now to FIG. 7, another preferred embodiment of the invention is shown in the form of a modified electrode termination pair 142. The electrode termination pair 142 includes a tip 144 and a ring 146. As shown in FIGS. 8A and 8B, the tip 144 and the ring 146 are formed on a single ceramic base structure 148. An electrically conductive coating 150 formed at the distal end of the base structure 148 provides the tip 144. An electrically conductive coating 152 formed at the proximal end of the base structure 148 provides the ring 146. The difference between FIGS. 8A and 8B is that both the inside and the outside surfaces of the ceramic base structure 148 are coated in FIG. 8A, whereas only the outer surface of the ceramic base structure 148 is coated in FIG. 8B.

While various embodiments of the invention have been shown and described, it should be apparent that many variations and alternative embodiments could be implemented in accordance with the invention. For example, although the ring 6 has been described as housing components such as the optical termination unit 24 and the opto-electrical transducer 26, these components could potentially be housed in the tip 4 if sufficient space is available within the tip interior. Other components, such as an R-wave amplifier and an electro-optical transducer for generating heartbeat monitoring signals could also be housed in the tip 4 if space permits. Another alternative would be to locate the optical termination unit 24 and the opto-electrical transducer 26 in the tip 4, while placing an R-wave amplifier and an electro-optical transducer in the ring 6. Additional functionality, such as a partial oxygen monitor, a core body temperature sensor, etc., may also be provided.

It is understood, therefore, that the invention is not to be in any way limited except in accordance with the spirit of the appended claims and their equivalents.

I claim:

1. A cardiac electrode termination pair system, comprising:

a tip, said tip including a bio-compatible ceramic base structure coated with a layer of electrically conductive material;

a ring, said ring including a bio-compatible ceramic base structure coated with a layer of electrically conductive material; and an insulative material disposed between said tip and said ring;

said coating layer on said tip being formed on outside and inside surfaces of said bio-compatible ceramic base structure associated therewith;

said coating layer on said ring being formed on outside and inside surfaces of said bio-compatible ceramic base structure associated therewith.

2. The system in accordance with claim 1, wherein said coating layer on said tip and said ring comprises a metal of low magnetic susceptance.

3. The system in accordance with claim 1, wherein said coating layer on said tip and said ring comprises a metal selected from the group consisting of platinum, titanium, and alloys thereof.

4. A cardiac electrode termination pair system, comprising:

a tip, said tip including a bio-compatible ceramic base structure coated with a layer of electrically conductive material;

a ring, said ring including a bio-compatible ceramic base structure coated with a layer of electrically conductive material; and an insulative material disposed between said tip and said ring;

said ceramic base structures of said tip and said ring being separate structures;

said insulative material being a stub separating said tip and said ring.

5. The system in accordance with claim 4, wherein said coating layer on said tip and said ring comprises a metal of low magnetic susceptance.

6. The system in accordance with claim 4, wherein said coating layer on said tip and said ring comprises a metal selected from the group consisting of platinum, titanium, and alloys thereof.

7. The system in accordance with claim 4, wherein said ring or said tip houses an optical termination and an opto-electrical transducer.

8. A cardiac electrode termination pair system, comprising:

a tip, said tip including a bio-compatible ceramic base structure coated with a layer of electrically conductive material;

a ring, said ring including a bio-compatible ceramic base structure coated with a layer of electrically conductive material; and an insulative material disposed between said tip and said ring;

said ceramic base structures of said ring and said tip being integrated as a single ceramic base structure;

said insulative material being an area of said single ceramic base structure.

9. The system in accordance with claim 8, wherein said coating layer on said tip and said ring comprises a metal of low magnetic susceptance.

10. The system in accordance with claim 8, wherein said coating layer on said tip and said ring comprises a metal selected from the group consisting of platinum, titanium, and alloys thereof.

* * * * *